US00PP19302P2

(12) United States Plant Patent
Fafard

(10) Patent No.: US PP19,302 P2
(45) Date of Patent: Oct. 7, 2008

(54) ***LIGULARIA* PLANT NAMED 'OSIRIS FANTAISIE'**

(50) Latin Name: *Ligularia dentara*
Varietal Denomination: Osiris Fantaisie

(76) Inventor: Serge Fafard, 818 rue Monique, St. Thomas de Joliette (CA), J0K 3L0

( * ) Notice: Subject to any disclaimer, the term of this patent is extended or adjusted under 35 U.S.C. 154(b) by 0 days.

(21) Appl. No.: 11/903,892

(22) Filed: Sep. 25, 2007

(51) Int. Cl.
*A01H 5/00* (2006.01)

(52) U.S. Cl. ..... Plt./448; Plt./263

(58) Field of Classification Search ..... Plt./448, Plt./263

See application file for complete search history.

*Primary Examiner*—Annette H Para
*Assistant Examiner*—S. B. McCormick-Ewoldt
(74) *Attorney, Agent, or Firm*—Penny J. Aguirre

(57) ABSTRACT

A new cultivar of *Ligularia dentata,* 'Osiris Fantaisie', characterized by its ovate-shaped leaves with margins that are incised, undulated, and often tripartite with conspicuous veining and purple-pink lower surfaces, its short plant height, and its cold hardiness in U.S.D.A. Zones 3.

2 Drawing Sheets

Botanical classification: *Ligularia dentata.*
Cultivar designation: 'Osiris Fantaisie'.

BACKGROUND OF THE INVENTION

The present invention relates to a new and distinct cultivar of *Ligularia dentata* and is hereinafter referred to by the cultivar name 'Osiris Fantaisie'.

The new cultivar resulted from an ongoing breeding project that commenced in 1994 in St-Thomas de Joliette, Quebec, Canada when the breeder discovered a unique seedling that arose from seed of *Ligularia* 'Othello' (not patented) in 1994. Multiple crosses and re-crosses made with this seedling and its progeny resulted in the selection of 'Osiris Fantaisie' in 2002.

Asexual reproduction of the new cultivar was first accomplished under direction of the inventor by in vitro propagation in Rijswijk, The Netherlands in December of 2004. Asexual reproduction of the new cultivar by division and tissue culture has shown that the unique features of 'Osiris Fantaisie' are stable and reproduced true to type in successive generations.

SUMMARY OF THE INVENTION

The following traits have been repeatedly observed with represent the characteristics of the new cultivar. These attributes in combination distinguish 'Osiris Fantaisie' as a new and unique cultivar of *Ligularia.*

1. 'Osiris Fantaisie' has leaves that are ovate in shape with undulating, incised margins, distinct veining, and a lower leaf surface that is flushed with red-purple.
2. 'Osiris Fantaisie' is short is stature with the foliage reaching a height of 60 cm (90 cm in bloom) in Quebec, Canada.
3. 'Osiris Fantaisie' has yellow-orange flowers in corymbs that arise above the foliage in late August to early October in Quebec, Canada.
4. 'Osiris Fantaisie' is cold hardy in U.S.D.A. Zone 3.

'Osiris Fantaisie' is a unique *Ligularia* and exhibits leaf characteristics that are unknown in other cultivars of *Ligularia* known to the inventor.

'Othello', a descendent in the breeding line of 'Osiris Fantaisie', differs from 'Osiris Fantaisie' in having leaves that are more kidney-shaped with margins that are finely serrated and lack undulations, in exhibiting smaller flowers, and is taller in height; reaching up to 1.5 m in height in bloom. 'Osiris Fantaisie' can also be compared to *Ligularia dentata* cultivars 'Desdemona' (unpatented) and 'Brit-Marie Crawford' (Plant Pat. No. 16,113). Both of these cultivars are similar to 'Osiris Fantaisie' in being short in stature and in having leaves that are tinted purple on the lower surface, however the leaves of 'Desdemona' and 'Brit-Marie Crawford' are kidney-shaped with margins that are less serrated, less undulated, and the upper surfaces of the leaves are brown-purple in color.

BRIEF DESCRIPTION OF THE DRAWING

The accompanying colored photographs illustrate the overall appearance and distinct characteristics of the 'Osiris Fantaisie' as grown in a trial bed in Quebec, Canada.

The photograph in the FIG. 1 was taken of a plant three years in age and the photographs in FIG. 2 and FIG. 3 were taken of plants five years in age.

DETAILED BOTANICAL DESCRIPTION OF THE PLANT

Figure 1:
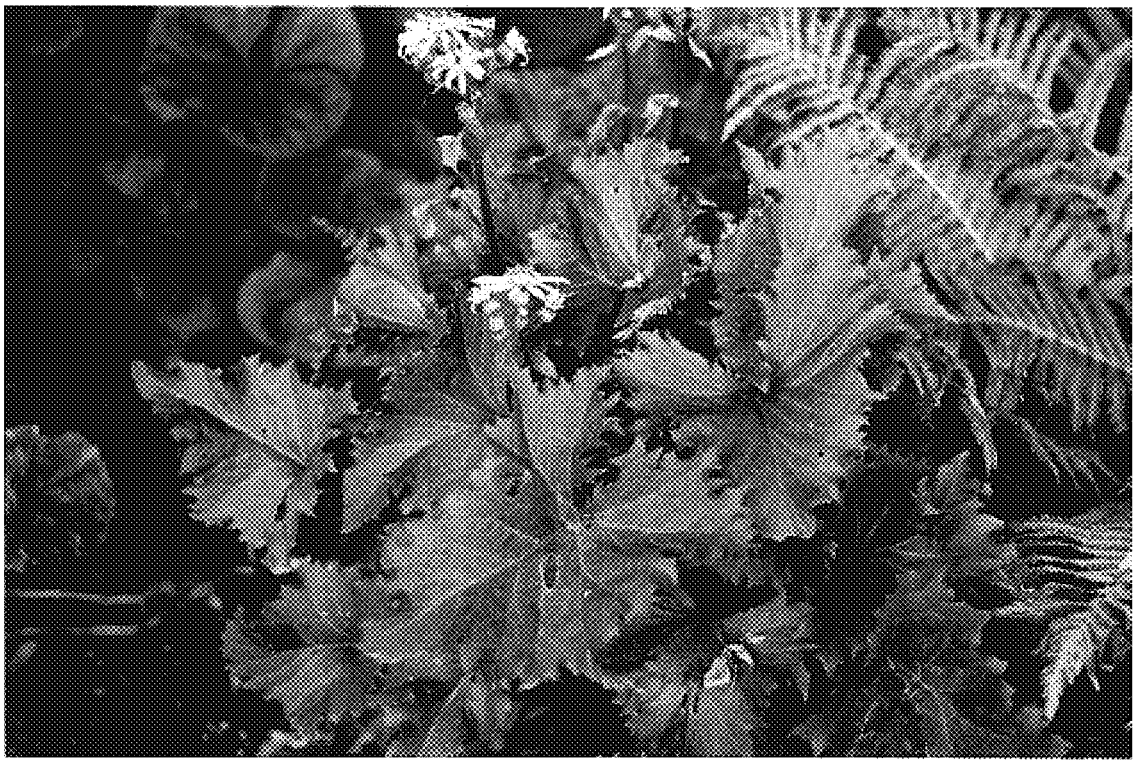
FIG. 1 provides a view of the habit and foliage characteristics of the new cultivar in bloom.
Figure 2:
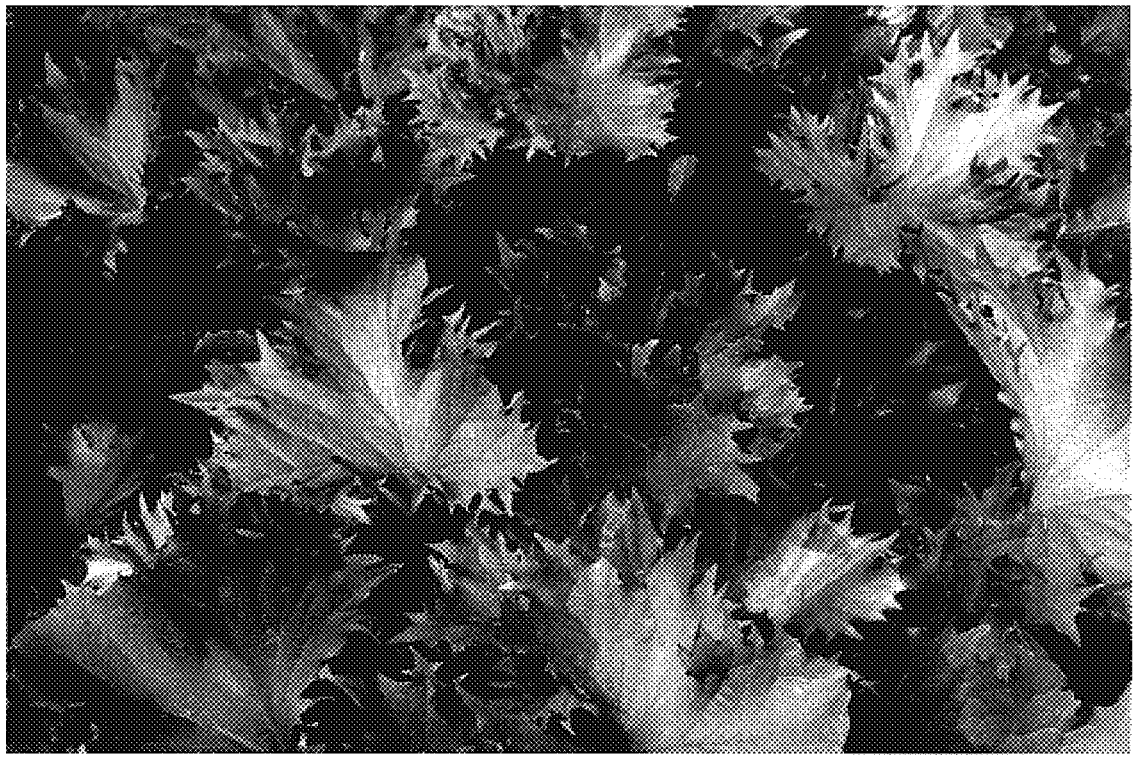
FIG. 2 shows a close-up view of the foliage.
Figure 3:
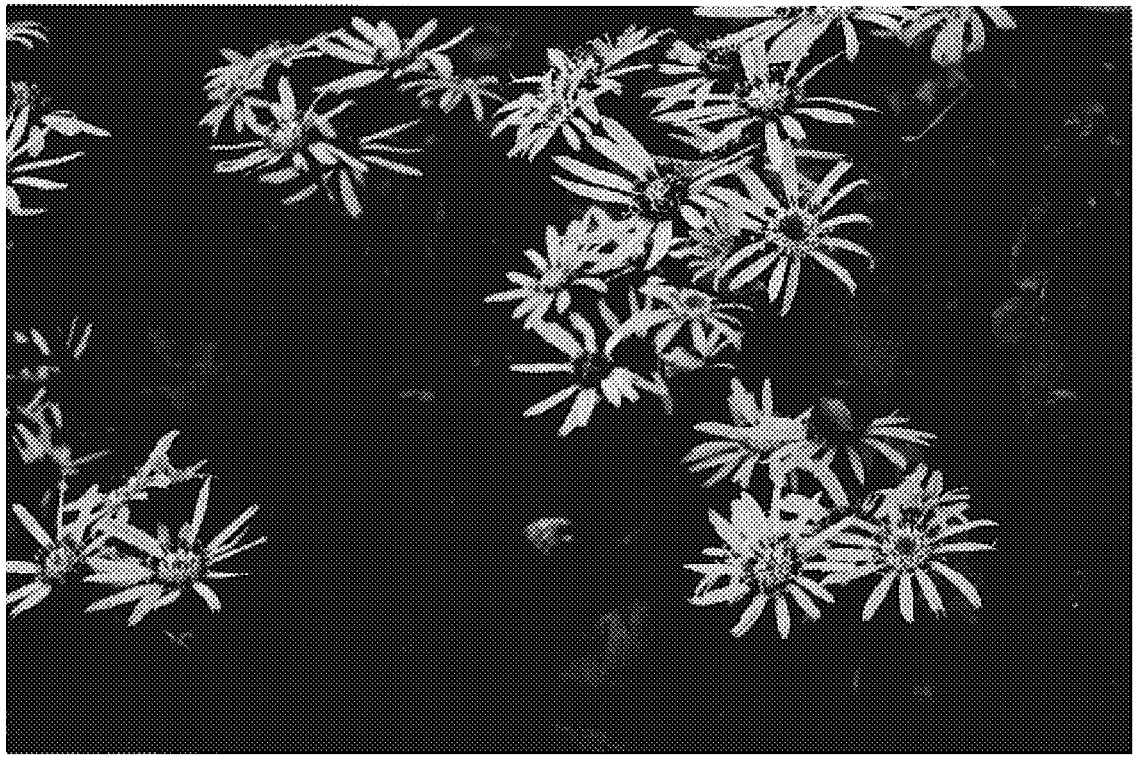
FIG. 3 provides a close-up view of the flowers. The colors in the photographs are as close as possible with the photographic and printing technology utilized. The color values cited in the detailed botanical description accurately describe the colors of the new *Ligularia.*

The following is a detailed description of plants of the new cultivar as grown outdoors in a trial sites in New Hope, Minn. for three years and in Quebec, Canada for five years.

The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General Description:

*Blooming habit.*—Blooms from late August to early October in Quebec, Canada.

*Plant habit.*—Clump-forming, robust, herbaceous perennial, vase-shaped, dwarf in comparison to other cultivars.

*Height and spread.*—Reaches about a height of about 60 cm (90 cm in height in bloom) and about 91 cm in width.

*Cold hardiness.*—U.S.D.A. Zone 3.

*Culture.*—Prefers full sun to dappled shade in moist, fertile soils.

*Diseases and pests.*—Disease and pest free under the conditions tested.

*Root description.*—Fibrous.

*Branching habit.*—Basal foliage on long petioles.

*Propagation.*—In vitro propagation is the preferred method, division are also possible.

*Growth rate.*—Moderate.

Foliage Description:

*Leaf shape.*—Broadly ovate.

*Leaf division.*—Simple.

*leaf base.*—Cuneate.

*Leaf apex.*—Acute.

*Leaf venation.*—Primary palmate, secondary net-veined, uniquely conspicuous, color on upper surface 144B in distal regions and 187D in mid region and near base of leaf, color on lower surface 187B to 187C.

*Leaf margins.*—Incised, often tripartite (oak-like), undulating.

*Leaf attachment.*—Petiolate.

*Leaf arrangement.*—Radicalis.

*Leaf orientation.*—Held about a 45° to petiole.

*Leaf surface.*—Glabrous on upper surface and puberulent but glossy in appearance on lower surface.

*Leaf color.*—Emerging leaves upper and lower surface: 178A to 178C, mature leaves upper surface; 137B to 137C becoming flushed with N186A, maturing leaves lower surface; 138C flushed with 178C.

*Leaf size.*—Matures to an average of 9 cm in length and 11 cm in width.

*Leaf quantity.*—New leaves continuously produced, about 12 by mid summer on two year-old plant.

*Petioles.*—Oval in shape, orientation ranges from vertical to a 45° angle, average of 24 cm in length and 4 mm in width, matures to 187A to 187B in color, surface is glabrous but sparsely covered with white hairs near leaf blade attachment.

Flower Description:

*Type.*—Capitulum, heterogamous with ray florets around the head margin and disk florets in the center, forming a radiant head, arranged in corymbs.

*Capitulum number.*—3 to 5 per peduncle branch, about 25 per flowering stem.

*Lastingness of inflorescence.*—3 to 4 weeks until senescence of ray florets, disk flowers are persistent, a cut flower will last about 10 days.

*Capitulum size.*—Matures to about 2 cm in depth and 7.3 cm in diameter, disk size is about 1.5 cm diameter.

*Fragrance.*—Slight rose scent.

*Phyllaries.*—About 16 arranged in a single row to form a campanulate involucre, about 1 cm in length and 2 mm in width, fused at base, acute apex, broadly lanceolate in shape, 138A to flushed with 178B in color, entire margin and glabrous on upper surface and hairy on inner surface.

*Buds.*—Cup-shaped, average of 1.5 cm in diameter and depth, phyllary are 138A to flushed with 178B and disk florets appear 178C in color when viewed in mass just prior to opening and short upright rays florets 15A with flushed of 34C.

*Peduncle.*—Branched, main peduncle about 45 cm in length and an average of 4 mm in width with 3 to 5 branches with an average of 10 cm in length and about 2.5 mm in width, 178A in color, texture is dull and sparsely covered with white hairs, one to two leaves, same coloration as basal leaves with petioles about 7 mm in length and 4 mm in width with leafy base and 187A to 187B in color.

*Pedicels.*—187A to 187B in color, an average of 5 cm in length and 2 mm in width, surface is dull and sparsely covered with fine white hairs.

*Ray Florets* (*female*).—Average of 11, oblanceolate in shape, vertical ridges on both surfaces, about 2.5 cm in length and 7 mm in width, emarginated apex, cuneate base, entire margin except apex, glabrous in texture, initially held upright about 70° from horizontal and become horizontal to reflexed as they mature, color of upper and lower surface when opening; 15A with an overlay of 34C changing to 15A, color of upper and lower surface when mature; 13C, pappus about 5 mm in length at apex of ovary.

*Disk flowers* (*bisexual*).—About 40, tubular in shape, arranged spirally on a conical receptacle, about 1.5 in length and 2 mm in width, pappus comprised of about 30 bristles about 7 mm in length and 178B in color; color emerges 15A flushed with 178C in color, mature florets color is defined by the reproductive organs extending beyond the apex of the floret, base of floret changing to a blend of N199C and 178A.

Reproductive Organs:

*Gynoecium.*—Pistil; 1, about 1.1 cm in length and 1.5 mm in width, style; 0.3 mm in width and 9 mm in length, 1C in color, surrounded by stamens, stigma; bifid, each arm is reflexed and about 2 mm in length and 14A in color, Ovary; inferior, and about 4 mm in length, 1 mm in width, and 145C in color.

*Androcoecium.*—Stamens; 4, un-fused, coherent in cylinder around style, anthers; 4 mm in length and 0.3 mm in width, basifixed, dehisced longitudinally, 200A in color filaments; 5 mm in length, 0.3 mm in width, 145C in color, pollen; abundant and 22A in color.

*Fruit.*—A terete with pappus, 199A in color.

It is claimed:

1. A new and distinct cultivar of *Ligularia* plant named 'Osiris Fantaisie' as herein illustrated and described.

* * * * *